(12) United States Patent
Rossi

(10) Patent No.: US 7,847,564 B2
(45) Date of Patent: Dec. 7, 2010

(54) CONDUCTIVITY PROBE AND DIALYSIS MACHINE COMPRISING THE PROBE

(75) Inventor: Vincenzo Rossi, Lippo di Calderara di Reno (IT)

(73) Assignee: Tecnologie Dinamiche S.A.S. di Rossi Vincenzo & C., Bologna (IT)

( * ) Notice: Subject to any disclaimer, the term of this patent is extended or adjusted under 35 U.S.C. 154(b) by 87 days.

(21) Appl. No.: 11/832,835

(22) Filed: Aug. 2, 2007

(65) Prior Publication Data
US 2008/0030204 A1    Feb. 7, 2008

(30) Foreign Application Priority Data
Aug. 4, 2006    (EP) ................... 06425569

(51) Int. Cl.
G01N 27/02    (2006.01)
G01R 27/08    (2006.01)
(52) U.S. Cl. .................. 324/630; 324/439; 324/696
(58) Field of Classification Search .............. 324/630, 324/439, 632, 696
See application file for complete search history.

(56) References Cited

U.S. PATENT DOCUMENTS

| | | | |
|---|---|---|---|
| 4,138,639 A * | 2/1979 | Hutchins | 324/442 |
| 4,420,752 A * | 12/1983 | Davis et al. | 340/870.17 |
| 5,619,722 A * | 4/1997 | Lovrenich | 710/2 |
| 5,674,404 A * | 10/1997 | Kenley et al. | 210/741 |
| 5,808,181 A * | 9/1998 | Wamsiedler et al. | 73/38 |
| 6,610,206 B1 * | 8/2003 | Callan et al. | 210/646 |
| 6,912,917 B2 * | 7/2005 | Brugger et al. | 73/861.08 |
| 7,057,400 B2 * | 6/2006 | Gaignet | 324/696 |

FOREIGN PATENT DOCUMENTS

IT    1 238 243 B    7/1993

* cited by examiner

Primary Examiner—Timothy J Dole
Assistant Examiner—Farhana Hoque
(74) Attorney, Agent, or Firm—Pearne & Gordon LLP

(57) ABSTRACT

A probe (1) for measuring the conductivity of a solution comprises a hydraulic part and an electronic part; the hydraulic part comprises a conduit (2) in the shape of a double tuning fork having an inlet (3) and an outlet (4) for the solution whose conductivity is to be measured; the electronic part comprises an energizing toroidal coil (7) and a receiving toroidal coil (22), both fitted round the conduit (2); the receiving coil (22) is mutually concatenated with the energizing coil (7) through an electromagnetic flux (F) generated by the energizing coil (7) in the respective toroid (T1) and through the solution circulating in the conduit (2); the probe (1) also comprises a feedback circuit (111) to keep the electromagnetic flux (F) constant.

20 Claims, 3 Drawing Sheets

CONDUCTIVITY PROBE AND DIALYSIS MACHINE COMPRISING THE PROBE

This invention relates to a probe for measuring electrical conductivity, in particular, a non-invasive probe for measuring the ionic conductivity of liquid solutions.

The invention also relates to a hemodialysis machine comprising the probe designed in particular for measuring the ionic conductivity of the solutions used.

In numerous fields of science and technology, for example the medical and zootechnical fields or even in the field of fuels, foodstuffs and oils, it is very important to closely monitor the conductivity of the solutions treated or used in order to guarantee the safety of the manufacturing processes involved.

Numerous measuring devices of substantially invasive type are known. These typically consist of a pair of electrodes of known surface area immersed to a predetermined depth in the solution to be examined.

The two electrodes are connected to a generator of a variable balanced voltage which causes alternating current to pass through them.

Basically, these devices measure the resistance of the solution (using a special type of Wheatstone bridge) from which the electrical conductivity of the solution can be derived.

One of the disadvantages of devices of this kind is due to the inevitable reaction of the electrodes with the solution in which they are immersed which leads to incrustation of the electrodes and contamination of the solution.

To overcome these disadvantages, a device for measuring electrical conductivity without electrodes immersed in the solution to be examined was devised in order to guarantee perfect galvanic isolation between the electrical components and the solution. This device is described in Italian patent IT-1238243 to the same Applicant as this invention.

The device comprises a substantially toroidal conduit made from an insulating, diamagnetic material that can be placed in a hydraulic circuit containing the solution whose electrical conductivity is to be measured.

Two coils are fitted around a section of the conduit.

One of the coils, used for energizing, is connected to a generator of a variable balanced voltage, while the second coil, used for receiving, is fitted in such a way as to be mutually concatenated with the energizing coil.

Thus, the current flowing through the second coil is proportional to the conductivity of the solution.

This device is not, however, free of disadvantages.

In particular, the device cannot measure conductivity of less than one milliSiemens.

Moreover, the current detected on the measuring coils depends on the inductance of the energizing coil through the current induced in the solution.

During use, the inductance tends to vary, thus varying the magnetic flux concatenated with the coil which in turn leads to variations in the induced current in the solution.

The difficulty of measuring low conductivity, especially in the order of microSiemens ($\mu S$) and milliSiemens (mS), means that this known device is not very versatile and cannot be fully relied on outside certain temperature ranges.

In this context, this invention has for its main technical purpose to provide a probe for measuring electrical conductivity in the order of milliSiemens and microSiemens.

Another aim of the invention is to provide a conductivity probe which can work at any temperature and which can guarantee satisfactory precision of measurement for each temperature value.

The technical purpose and aims specified are substantially achieved by a conductivity probe comprising the technical characteristics described in claim 1 and in one or more of the claims dependent thereon.

Further features and advantages of this invention are more apparent in the detailed description below, with reference to a preferred, non-limiting, embodiment of conductivity probe illustrated in the accompanying drawings, in which.

Figure 1:
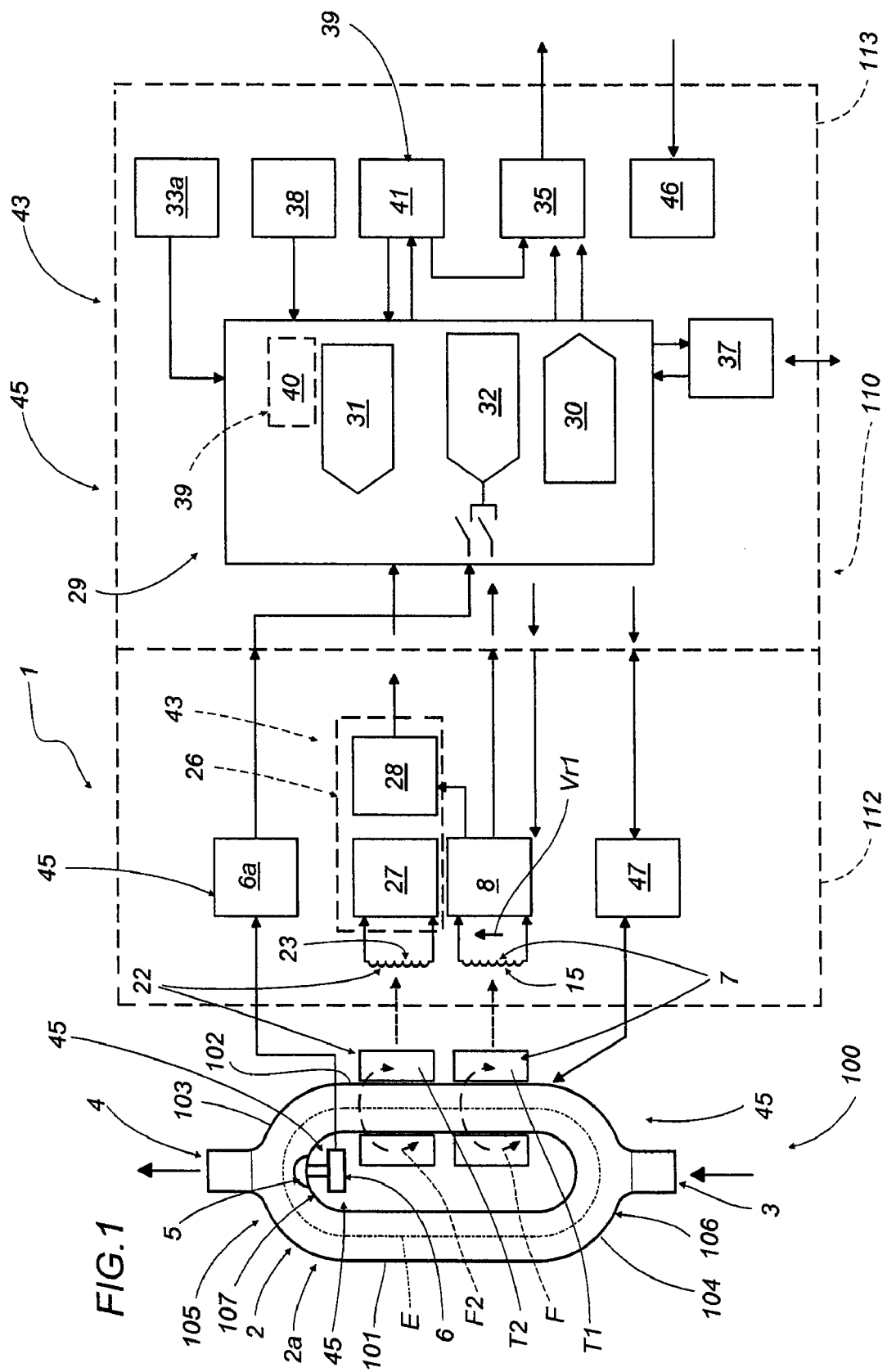
FIG. 1 is a highly schematic view, partly in blocks and with some parts cut away for clarity, of a conductivity probe according to the invention.

With reference to the accompanying drawings, in particular FIG. 1, the numeral 1 denotes a conductivity probe for measuring the conductivity of a solution.

The probe 1 comprises a hydraulic part 100 associated with an electronic part 110 that act in conjunction to calculate the conductivity.

The hydraulic part 100 comprises a conduit 2 having a first and a second section 101, 102, substantially straight and parallel to each other.

The first and second straight sections 101, 102 are joined to each other by a first and a second curved section 103, 104 to form a closed loop.

In other words, the conduit 2 is defined by a first portion 105 in the shape of a tuning fork and a second portion 106 in the shape of a tuning fork joined at the ends of the respective prongs.

The conduit 2 has an inlet 3 and an outlet 4 and forms a measuring cell 2a for the probe 1.

Figure 3:
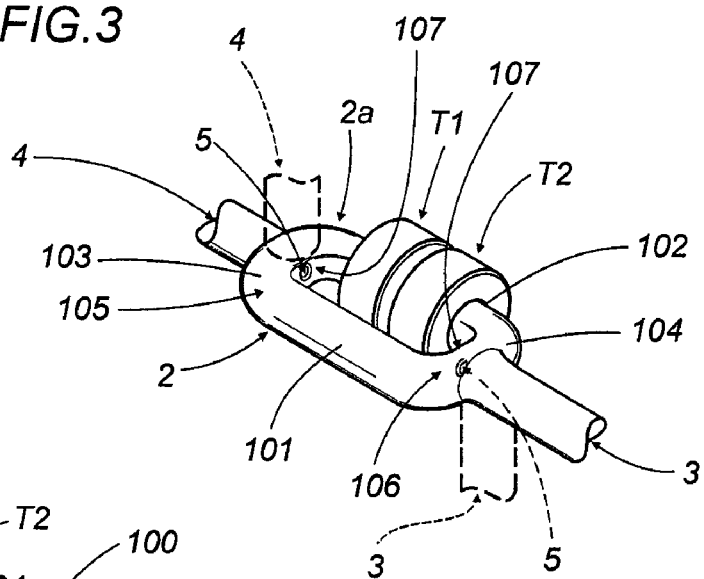
FIG. 3 is a perspective view of a measuring cell of the probe of FIG. 1.

FIG. 3 in particular shows how the inlet 3 and the outlet 4 may be oriented in any direction with respect to the conduit 2.

Specifically, the dashed line shows the inlet 3 and the outlet 4 oriented in a substantially perpendicular direction and positioned on opposite sides of the plane in which the conduit 2 lies.

It should also be observed that the terms inlet 3 and outlet 4 are used arbitrarily for the sake of simplicity since the probe 1 works in exactly the same way whether the solution flows from the inlet 3 towards the outlet 4 or in the other direction.

The conduit 2 is designed to be crossed by the solution whose conductivity is to be measured.

The conduit 2 is made preferably of Duran® glass whose physical and chemical properties are unalterable over time.

Also, glass of this type is not affected by liquids circulating inside the conduit 2.

In particular, Duran® glass advantageously enables the probe 1 to be used in dialysis machines.

Further, the conduit 2 is preferably made as a single part with an uninterrupted weld seam between the first and the second tuning fork shaped portion 105, 106.

The conduit 2 has a recess 5 for housing a temperature transducer 6 designed to measure the temperature of the solution flowing through the conduit 2 but without coming into contact with it.

Thus, the temperature is measured non-invasively, without contact between the transducer 6 and the solution in the conduit 2.

It should be observed that placing the thermistor 6 in the recess 5 prevents wear of the thermistor 6 and contamination of the solution.

With reference in particular to FIG. 1, it is important to note that the recess 5 is made preferably in one of the two curved sections 103, 104.

Figure 4:
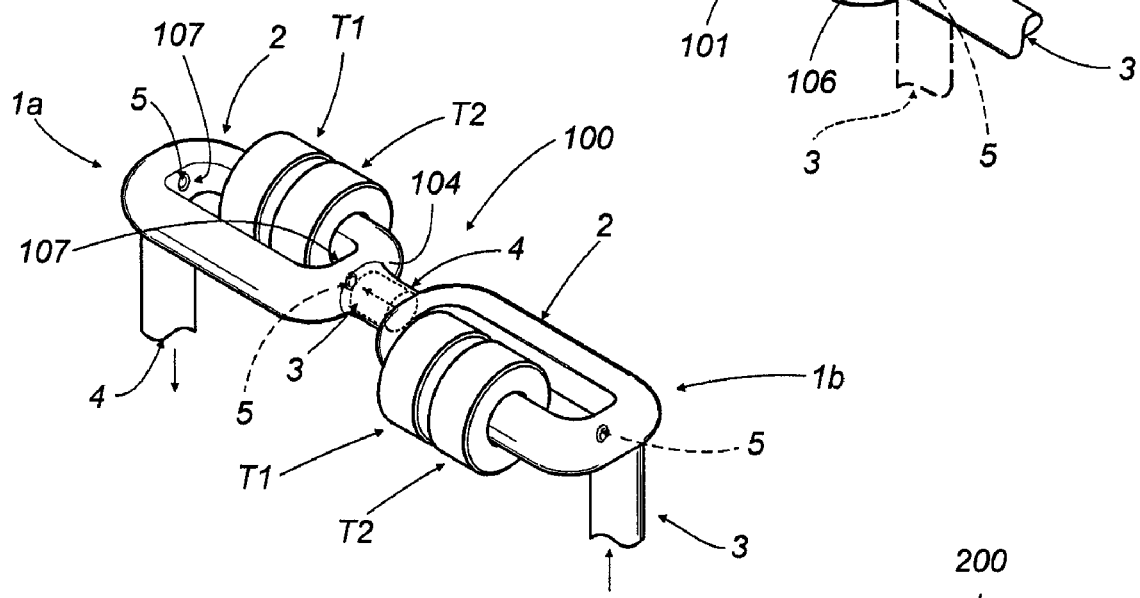
FIG. 4 is a perspective view of another embodiment of a measuring cell of the probe according to the invention.
Figure 5:
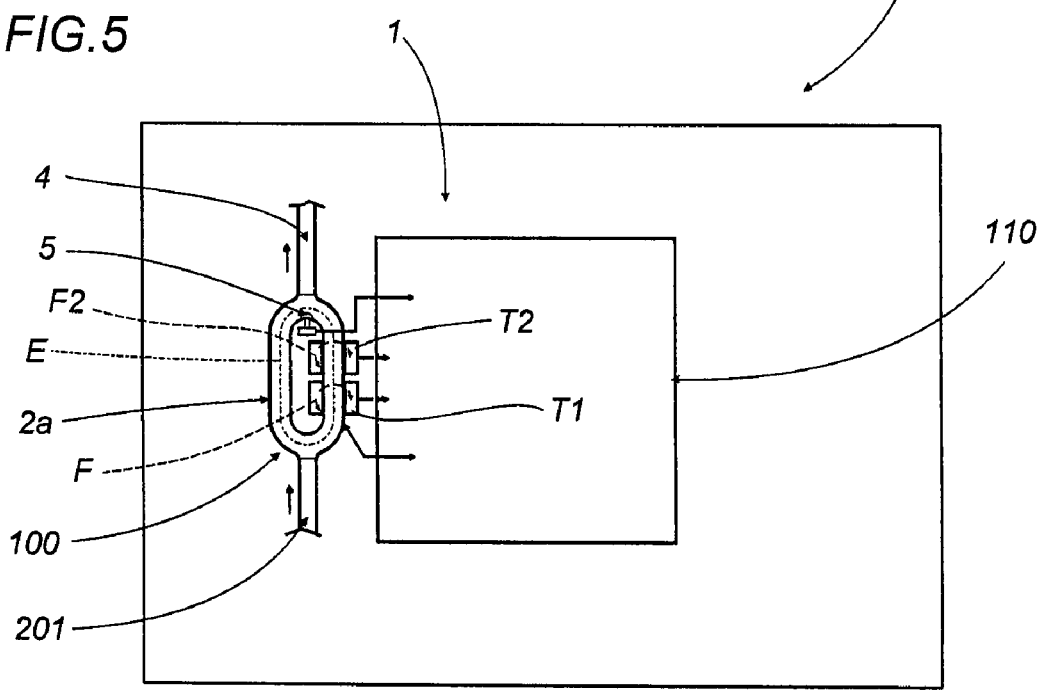
FIG. 5 is a schematic view of a dialysis machine according to the invention.

Specifically, the recess 5 is made in a concave portion 107 of the curved section 103, 104, as also shown by way of example by the dashed line in FIGS. 3 and 4.

Further, the recess 5 is preferably located in front of the inlet 3 or outlet 4 so as to cause a minimum or substantially zero turbulence in the flow of the solution in the cell 2a.

The electronic part 110 comprises a probe 1 amplifying and drive circuit 112.

The circuit 112 comprises a front end 6a of substantially known type, not described in any detail, for acquiring the temperature and associated with the transducer 6.

The circuit 112 also comprises a primary or energizing toroidal coil 7 fitted round the conduit 2 and a supply circuit 8 for energizing the coil 7.

Figure 2:
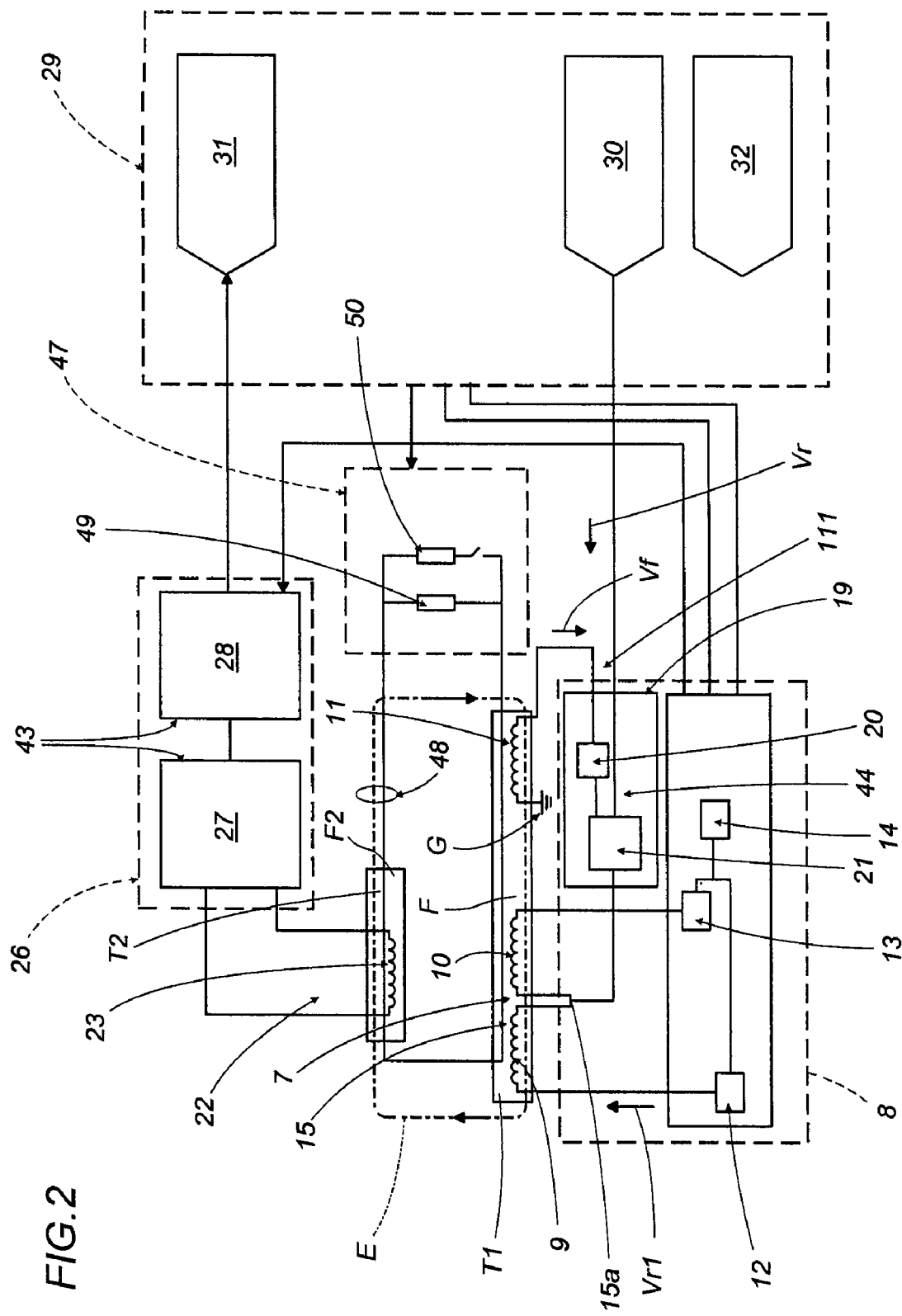
FIG. 2 is a schematic view with some parts cut away for clarity, of a first detail of the circuitry of the probe of FIG. 1.

Looking more closely at the details with reference in particular to FIG. 2, the energizing coil 7 comprises three windings 9, 10 and 11 around the toroid T1.

Of the three windings 9, 10, 11 around the toroid T1, the windings 9 and 10 have the same number S of spirals, while the winding 11 has S1 spirals.

The windings 9 and 10 are connected in series and essentially constitute a single energizing winding 15.

The winding 11 has an induced current flowing through it and constitutes a feedback winding, as explained in more detail below.

The supply circuit 8 comprises two modulators 12 and 13, of substantially known type and therefore not described in detail, and a device 14 for driving them, such as, for example, a square wave oscillator with a duty cycle of 50%.

The modulators 12 and 13 are connected to the winding 15 to energize the coil 7 to a voltage Vr1.

The windings 9 and 10 are energized alternately by the modulators 12 and 13 to produce in the coil 7 an alternating electromagnetic flux F as a function of the number S of turns S in each of the windings 9 and 10, of the supply voltage Vr1 and of the supply voltage frequency.

The probe 1 comprises a feedback circuit 111 comprising the feedback winding 11 which is magnetically coupled with the winding 15 through the toroid T1 and which, by effect of the electromagnetic flux F, has across its ends a voltage Vf proportional to Vr1 in a ratio of S/S1 and with a coupling or mutual induction coefficient.

The feedback circuit 111 also comprises a regulator 19 to generate and stabilize the voltage Vr1.

The regulator 19 receives as input the above mentioned voltage Vf and an applied voltage Vr and, based on these voltages, modulates the voltage Vr1 at an intermediate portion 15a of the winding 15.

In short, the regulator 19 provides feedback that controls the supply to the winding 15 by regulating the voltage Vr1 as a function of the applied voltage Vr and of the voltage Vf measured across the ends of the feedback winding 11.

Specifically, the regulator 19 comprises a rectifier 20 and an integrator 21 to modulate the voltage Vr1.

The rectifier 20 rectifies the voltage Vf and applies it to the input of the integrator 21 which also receives the voltage Vr as input and stabilizes the output voltage Vr1 according to the set reference value Vr.

Basically, the voltage Vf constitutes a coil 7 supply control parameter and is measured, for example, in relation to a known reference G.

A secondary or receiving toroidal coil 22 is also fitted round the conduit 2 and is positioned in such a way as to be mutually concatenated or mutually induced with the coil 7.

It should be noticed that the coil 22 and the coil 7 are fitted coaxially round the straight section 102 of the conduit 2.

As illustrated, the coil 22 comprises a winding 23 around a toroid T2.

The amplifying and drive circuit 112 comprises a current reading device 26, associated with the coil 22, for measuring an induced current I in the coil 22 itself when the energizing coil 7 is energized.

Looking in more detail, the device 26 comprises an amplifier 27 and a rectifier 28, consisting, for example, of a synchronous rectifier.

Notice that the synchronous rectifier 28 is preferably synchronised, in substantially known manner, with the above mentioned energizing circuit 8.

The electronic part 110 comprises a probe 1 processing and control system 113 in communication with the amplifying and drive circuit 112.

With reference in particular to FIGS. 1 and 2, the processing and control system 113 comprises a computerized control unit 29 in communication with the coil 7 supply circuit 8, with the temperature transducer 6 through the front end 6a and with the device 26 for reading the current I at the ends of the coil 22.

More specifically, the unit 29 comprises a digital/analog converter 30 for generating the reference voltage Vr to energize the coil 7 and an analog/digital converter 31 used solely to convert the current I flowing in the coil 22, amplified and rectified by the device 26.

The unit 29 also comprises an analog/digital converter 32 for acquiring the temperature values measured by the transducer 6.

For example, and without restricting the scope of the invention, the converter 31 may be of the 24-bit type, while the converters 30 and 32 may, respectively, be of the 12- and 16-bit types.

The unit 29 provides as output the reference voltage Vr and the commands for the device 14.

The unit 29 supervises the control of the probe 1 and, specifically, the calculation of conductivity as a function of solution temperature and of the current I measured in the coil 22.

The unit 29 comprises a counter 33a for scanning the measurement time intervals.

With reference to FIG. 1 in particular, the processing and control system 113 comprises an analog frequency output and an analog voltage output, schematically illustrated as a block 35, to provide as an output the calculated conductivity value. Both the voltage and frequency values indicated are proportional to the calculated conductivity and indicative of the same.

The conductivity measurement processed by the program residing in the computerized unit 29 is therefore made available to the user in analog form and compensated in temperature.

It should be noticed that, preferably, the block 35 is galvanically isolated and protected against short circuiting.

The system 113 also comprises a serial communications port 37, for example of the substantially known RS-232, RS-485, RS-422, I2C bus or SPI type, to make the calculated quantities available for further applications, which are not described since they are outside the scope of this invention, and to receive as input instructions for the probe 1.

An automatic device 38 of substantially known type forming part of the unit 29 generates a voltage reference for operating the converters 30, 31 and 32.

The probe 1 comprises a safety system 39 for indicating faults that may occur in the probe 1 during the operation described below.

For example, the system 39 indicates malfunctioning of the device 14, exceeding of a set range or incorrect conversions of the current I and of the solution temperature, processing errors when calculating the conductivity, errors when the generating the voltage reference for the converters 30, 31 and 32 and malfunctioning of the device 33a.

The system 39 comprises a first, internal watchdog 40 and a second, external watchdog 41, the term "watchdog" meaning a hardware tool which monitors the probe 1 to ensure it is always in good working order.

Preferably, the electronic part 110 also comprises a power supply block 46 equipped with resettable fuses that are not illustrated.

The above mentioned amplifying and drive circuit 112 preferably comprises a test circuit 47 through which the energizing coil 7 is coupled with the secondary coil 22.

As better illustrated in FIG. 2, the test circuit 47 comprises a spiral 48, which is magnetically coupled with the coil 22, and a bias resistor 49.

The test circuit 47 also comprises a test resistor 50 connectable in parallel with the bias resistor 49.

The circuit 47 enables the receiving coil 22 to be energized with a current that cancels its magnetizing current. The spiral 48 and the bias resistor 49 draw from the coil 7 a current proportional to the value of the resistor 49 that induces the required function in the coil 22.

By connecting the test resistor 50 in parallel with the bias resistor 49, a known current is added to the circuit in such a way as to test the measuring cell.

In use, the primary coil 7 is energized with an alternating voltage and the current I proportional to the conductivity is measured on the secondary coil 22.

More specifically, the coil 7 is supplied using the regulator 19 to regulate the alternating voltage Vr1 applied to the winding 15 through the modulators 12 and 13.

It should be noticed that the feedback control is performed by the feedback circuit 111 on the voltage Vr1 in such a way as to keep the above mentioned magnetic flux F generated by the toroid T1 constant while the inductance of the coil 7 changes over time.

In particular, the inductance of the coil 7 may vary with changes in operating conditions.

A variable electrical field E proportional to the electromagnetic flux F is created at the centre of the coil 7, that is to say, in the solution circulating in the conduit 2.

The ions in the solution, like a resistor, allow the passage of a current which increases as the concentration of the ions in the solution increases (on account of the reduced electrical resistance).

The alternating current circulating in the solution also flows through the coil 22, thus inducing a magnetic flux F2 in the toroid T2 and producing the current I at the ends of the winding 23.

As mentioned above, the energizing coil 7 supply frequency is generated by the computerized unit 29 through the device 14: for example, a PWM module with a duty cycle of 50%.

It should be noted that the supply frequency may be differentiated to reduce the interference between primary and secondary and between probes 1 that are near each other.

For calculating the conductivity, the current I at the ends of the coil 22 is digitized by the converter 31, thus obtaining a digital signal, expressed in bits, relating to the conductivity.

The computerized unit 29 applies an offset and gain correction to the digital signal and returns the conductivity value in Siemens or submultiples thereof.

For example, a conversion law such as:

$$C1 = \pm K \times (C-O)$$

where C is the value of the digital signal, O the value in bits with an empty probe 1, that is to say, an offset correction, and C1 the conductivity value, for example in $\mu S/cm$, since K is the transformation constant for converting bits into $\mu S/cm$.

The offset correction may be obtained with an empty probe calibration procedure initially providing an offset of 0.

Advantageously, in alternative embodiments that are not described, other conversion laws may be used to obtain a conductivity value in Siemens.

The transformation constant K takes into account the following: ratio of energizing coil 7 spirals to receiving coil 22 spirals; cell constant; and amplifications required to condition the signal.

In calculating the conductivity of the solution, the computerized unit 29 also weights the conductivity value as a function of the temperature measured by the transducer 6.

The safety system 39 issues an instant warning in the event of any malfunction and the internal watchdog 40 periodically tests the efficiency of the hardware.

Any fault in the internal watchdog 40 is detected and indicated by the external watchdog 41.

The amplifier 27, the rectifier 28 and the unit 29 constitute means 43 for reading a current.

The feedback winding 11, the rectifier 20 and the integrator 21 constitute compensation means 44, in particular, means 44 for compensating an electromotive force (emf), the term "electromotive force" being used to mean a force that produces a current in a conductor.

The transducer 6, the front end 6a for acquiring the temperature and the computerized control unit 29 constitute temperature detection means 45.

This invention also applies to a double probe comprising a first and a second probe 1 as described above mounted in series, that is to say, with the outlet 4 of the load cell of one associated with the inlet 3 of the load cell of the other.

FIG. 4 in particular shows a measuring cell 100 made as a single part defined by the conduit 2 of a first probe 1a connected to the conduit 2 of a second probe 1b.

Specifically, the outlet 4 of the conduit 2 of the first probe 1a is connected to the inlet 3 of the conduit 2 of the second probe 1b.

The first and second probes 1a, 1b have respective toroids T1 and T2 to which the respective electronic circuits (not illustrated) are interconnected.

Advantageously, the probes 1a and 1b are separate and the operation of one independent of that of the other.

The first and second probes 1a, 1b form a redundant system to increase the safety level and measurement certainty especially in medical applications.

As illustrated in FIG. 6, this invention also relates to a hemodialysis machine 200 comprising a conductivity probe 1 as described above.

The machine 200 is of substantially known type and therefore not described in detail. The machine 200 comprises a hydraulic circuit 201 including the measuring cell 2a of the conductivity probe 1. As described above, the cell 2a is associated with the electronic part 110 of the probe 1.

The invention has important advantages.

The conductivity value calculated is substantially free of temperature related errors and hence can be very accurate.

The feedback control of the induced electromagnetic flux in the toroid T1 ensures that the current I measured in the coil 22 depends solely on the solution and on the input quantities and not on alterations of the energizing coil 7.

Indeed, the temperature of the energizing coil during operation may be such as to vary the inductance of the coil itself, thus causing measurement errors: the feedback circuit allows these errors to be corrected.

The conductivity calculation is extremely precise and makes it possible to measure conductivity in the order of microSiemens and nanoSiemens.

Advantageously, moreover, the probe may be used for all those applications where conductivity must be measured non-invasively such as, for example, in the zootechnical, food, fuel and oil industries, or where infinitesimal measurements of conductivity are required.

In particular, the conductivity probe can be advantageously applied to dialysis where the conductivity of the solutions used may vary in a range from approximately 5 μSiemens to approximately 20 mSiemens.

Further, electronic control of the probe means that the probe can be used under different temperature conditions.

The temperature transducer mounted inside a specially-made recess enables the probe to operate in a totally non-invasive manner, preventing the probe from contaminating the solution to be measured.

Furthermore, the double probe has the added advantage of guaranteeing a higher safety level thanks to the redundancy of the two probes arranged in series.

The invention described has evident industrial applications and can be modified and adapted in several ways without thereby departing from the scope of the inventive concept. Moreover, all the details of the invention may be substituted by technically equivalent elements.

The invention claimed is:

1. A probe for measuring the conductivity of a solution, comprising an annular conduit (2) having an inlet (3) and an outlet (4) for the solution and forming a cell (2a) for measuring the conductivity, a first and a second coil (7, 22) fitted round the conduit (2), an energizing circuit (8) that generates a voltage (Vr1) for energizing the first coil (7), current reading means (43) associated with the second coil (22) for reading a current (I) circulating in the second coil (22), the second coil (22) being mutually concatenated with the first coil (7) through an electromagnetic flux (F) generated by the first coil (7) and through the solution circulating in the conduit (2), the probe being characterized in that it comprises: a temperature transducer (6) for sensing a temperature of the solution within the conduit (2) at a location where the solution experiences a minimum turbulence; a feedback winding (11) in which an electric current is induced by the electromagnetic flux (F) generated by the first coil (7); and compensation means (44) associated with the first coil (7) to perform a comparison of a reference voltage (Vr) to a feedback voltage (Vf) across the feedback winding (11) and vary the voltage (Vr1) generated by the energizing circuit (8) based on the comparison to maintain the electromagnetic flux (F) generated by the first coil (7) at a substantially-constant value, the compensation means (44) comprising a computerized unit (29) for determining an offset correction to the conductivity value measured with the cell (2a) as a function of the temperature of the solution as sensed by the temperature transducer (6) to output a calibrated conductivity value that is a function of both the temperature of the solution and the feedback voltage (Vf) across the feedback winding (11).

2. The probe according to claim 1, characterized in that the compensation means (44) comprise a feedback circuit (111) coupled with the electromagnetic flux (F) and a regulator (19).

3. The probe according to claim 2, characterized in that the computerized control unit (29) for supplying to the regulator (19) a reference voltage (Vr) to energize the first coil (7), the regulator (19) receiving as input both the voltage (Vf) measured at the ends of the feedback winding (11) and the reference voltage (Vr) and providing feedback used to regulate the energizing voltage (Vr1).

4. The probe according to claim 3, characterized in that the regulator (19) comprises an integrator (21) for comparing the voltage (Vf) measured at the ends of the feedback winding (11) with the reference voltage (Vr).

5. The probe according to claim 2, characterized in that the regulator (19) comprises a rectifier (20) for rectifying the voltage (Vf).

6. The probe according claim 1, characterized in that the conduit (2) has a recess (5) and the temperature transducer (6) is mounted in the recess and kept separate from the solution, for measuring the temperature of the solution, wherein the recess is formed in the conduit (2) at a location adjacent to an intersection between two branches of the conduit to minimize turbulence induced by the recess in the solution.

7. The probe according to claim 6, characterized in that the computerized control unit (29) associated with the temperature transducer (6) and with the reading means (43) for calculating the conductivity of the solution as a function of the current (I) and temperature of the solution.

8. The probe according to claim 1, characterized in that the conduit (2) is defined by a first portion (105) in the shape of a tuning fork and a second portion (106) in the shape of a tuning fork joined at the ends of the respective prongs, the first and the second coil (7, 22) being preferably fitted round a straight section (103, 104) of the conduit (2).

9. The probe according to claim 8, characterized in that the recess (5) is made in a concave portion (107) of a curved section (103, 104) of the conduit (2).

10. The probe according to claim 1, characterized in that it comprises a safety system (39), associated with the computerized unit (29), for indicating faults that may occur in the probe.

11. The probe according to claim 1, characterized in that the annular conduit (2) is made as a single part.

12. The probe according to claim 1, characterized in that it comprises an analog frequency output (35).

13. The probe according to claim 1, characterized in that it comprises an analog voltage output (36).

14. The probe according to claim 1, characterized in that it comprises a serial communications port (37).

15. The probe according to claim 1, characterized in that it comprises a test circuit (47) acting between the first and the second coil (7, 22) to ensure that the first and second coils (7, 22) are correctly coupled with each other.

16. A double probe for measuring the conductivity of a solution, characterized in that it comprises a first probe (1a) and a second probe (1b) according to claim 1, coupled with each other in such a way that the outlet (4) of the conduit (2) of the first probe flows into the inlet (3) of the conduit (2) of the second probe to form a single measuring cell (100), thus obtaining a redundant conductivity measurement for the solution flowing through the first and the second probe (1a, 1b).

17. The double probe according to claim 16, characterized in that the measuring cell (100) is made as a single part.

18. A dialysis machine comprising a hydraulic circuit (201) for circulating a solution, characterized in that it comprises a conductivity probe (1) or a double probe according to claim 1, the measuring cell (2a, 100) being located in the hydraulic circuit (201).

19. A probe for measuring the conductivity of a solution, comprising an annular conduit (2) having an inlet (3) and an outlet (4) for the solution, a first and a second coil (7, 22) fitted round the conduit (2), an energizing circuit (8) that generates a voltage (Vr1) for energizing the first coil (7), current reading means (43) for reading a current (I) circulating in the second coil (22), a feedback coil (11) across which a voltage (Vf) is induced in response to the energizing of the first coil (7), a temperature transducer (6) for sensing a temperature of the solution within the conduit (2) at a location where the solution experiences a minimum turbulence, compensation means (44) for adjusting the voltage (Vr1) for energizing the first coil based on the voltage (Vf) induced to maintain a substantially-constant electromagnetic flux (F) generated by the first coil (7), and a computerized control unit (29) for compensating the conductivity of the solution based on a temperature of the solution as measured by the temperature transducer (6), the second coil (22) being mutually concatenated with the first coil (7) through the electromagnetic flux (F) generated by the first coil (7) and through the solution, the probe being characterized in that the conduit (2) has a recess (5) and the temperature transducer (6) is mounted in the recess and kept separate from the solution, for measuring the temperature of the solution.

20. A probe for measuring the conductivity of a solution, comprising an annular conduit (2) having an inlet (3) and an outlet (4) for the solution and forming a cell (2a) for measuring the conductivity, a first and a second coil (7, 22) fitted round the conduit (2), an energizing circuit (8) that generates a voltage (Vr1) for energizing the first coil (7), current reading means (43) associated with the second coil (22) for reading a current (I) circulating in the second coil (22), the second coil (22) being mutually concatenated with the first coil (7) through an electromagnetic flux (F) generated by the first coil (7) and through the solution circulating in the conduit (2), the probe being characterized in that it comprises compensation means (44) associated with the first coil (7) to keep the electromagnetic flux (F) constant, wherein the conduit (2) has a recess (5) and a temperature transducer (6) mounted in the recess and kept separate from the solution, for measuring the temperature of the solution, the temperature transducer (6) being disposed to measure a solution temperature at a location within the annular conduit where the solution exhibits minimal turbulence.

* * * * *